United States Patent [19]

Al-Sioufi et al.

[11] Patent Number: 5,062,837
[45] Date of Patent: Nov. 5, 1991

[54] IV NEEDLE HOLDER

[76] Inventors: Habib Al-Sioufi, P.O. Box 654, Brookline, Mass. 02146; Antoine J. Koudsi, 52 Blueberry Circle, Pelham, N.H. 03076

[21] Appl. No.: 528,082

[22] Filed: May 24, 1990

Related U.S. Application Data

[62] Division of Ser. No. 186,432, Apr. 26, 1988, Pat. No. 4,942,881.

[51] Int. Cl.⁵ ............................................. A61M 5/00
[52] U.S. Cl. .................................... 604/240; 128/763
[58] Field of Search ............................ 128/763–766; 604/240

[56] References Cited

U.S. PATENT DOCUMENTS

| 4,822,343 | 4/1989 | Beiser | 128/763 |
| 4,841,985 | 6/1989 | Wanamaker | 604/240 |

FOREIGN PATENT DOCUMENTS

| 2564726 | 11/1985 | France | 128/763 |
| 0801838 | 2/1981 | U.S.S.R. | 604/240 |

Primary Examiner—Max Hindenburg
Attorney, Agent, or Firm—James J. Brown

[57] ABSTRACT

A blood collection needle holder is described which permits quick release of a spent blood collection needle once it has been used without complex manipulation by the health care provider. The device provides a locking mechanism on one end of a needle and blood collection container holder which can be opened with the fingers of one hand in order to avoid time consuming and potentially hazardous manipulations.

4 Claims, 5 Drawing Sheets

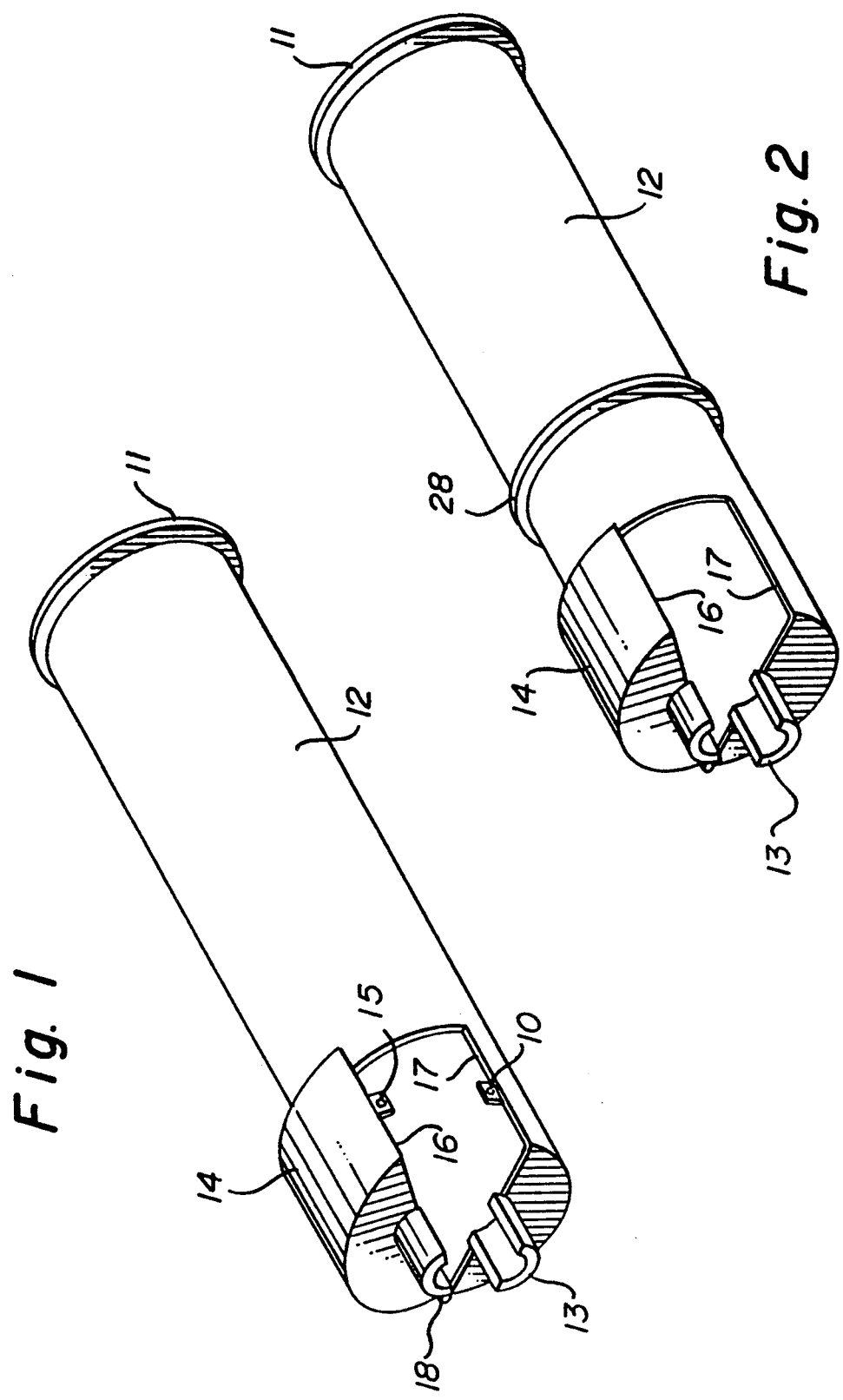

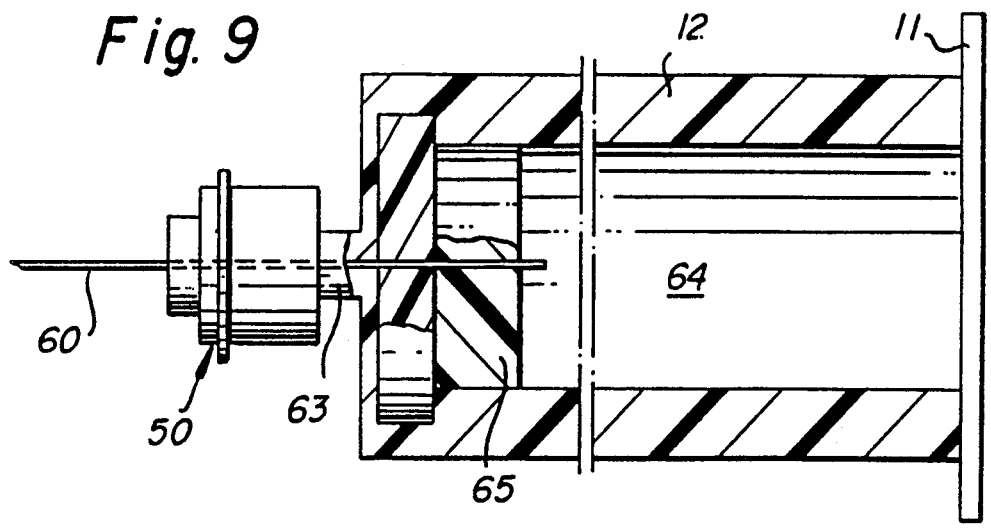
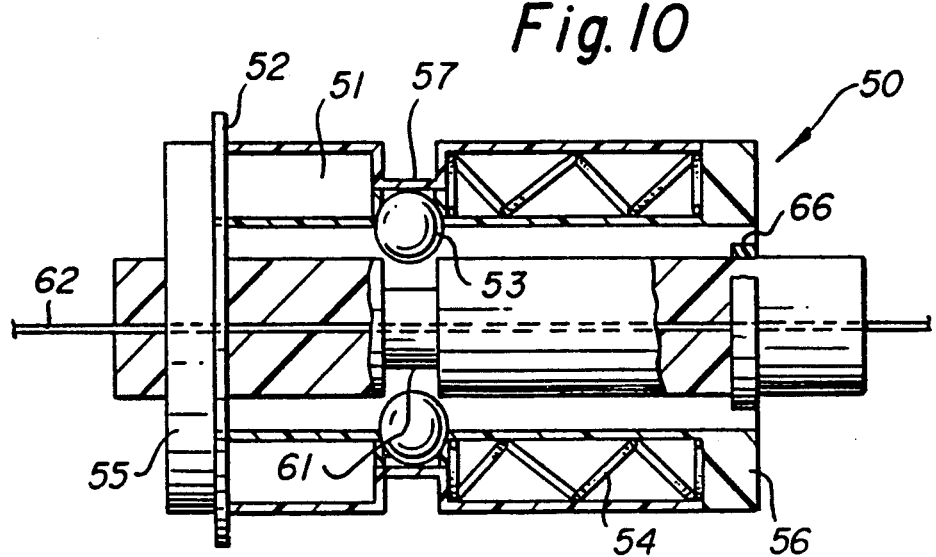
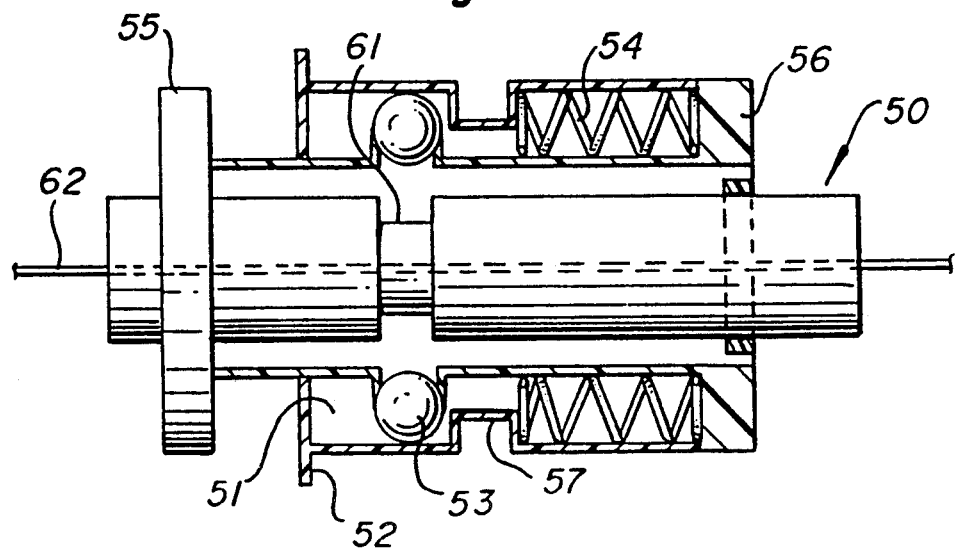

IV NEEDLE HOLDER

This is a division of application Ser. No. 07/186,432, filed Apr. 26, 1988, now U.S. Pat. No. 4,942,881.

SUMMARY OF THE INVENTION

The present invention is directed to a blood collection needle holder with improved means for disposing of the blood collection needle without requiring difficult manipulation or the use of external devices. More specifically, the present invention is concerned with a blood collection needle holder having a locking provision for releaseably holding the blood collection needle in communication with a collection container which is disposed within the holder and for permitting the used needle to be discarded easily and quickly while avoiding contact with the used needle by the health care provider.

BACKGROUND OF THE INVENTION

The use of disposable blood collection and other intravenous systems has become commonplace. Typical of such systems for example are those which use disposable blood collection needles which are attached to reusable holders for blood collection tubes. Frequently, for example, the blood collection tube fits within the holder and has a rubber stopper which is penetrated by one end of the blood collection needle once the other end of the blood collection needle has been inserted into a vein. These systems also can employ sterile disposable adapters which are designed to allow the use of a variety of attachments such as catheters, tubes, for example.

One of the drawbacks of such systems, however, is that a certain degree of time consuming and hazardous manipulation is required in order to remove the used blood collection needle from the holder and replace it with another blood collection needle. This manipulation may for example involve unscrewing the blood collection needle from the holder. Such manipulation has become a more acute problem in recent years with the advent and recognition of contageous diseases with are transmitted through the blood stream. Thus, health care provider using such blood collection equipment is put to the hazard of accidentally being pricked with the used blood collection needle when it is attempted to remove the needle from the blood collection system. Further, although somewhat less serious a problem, the removal of the used blood collection needle from the holder is time consuming since it requires a relatively complex motion to unscrew the used needle.

It is accordingly an object of the present invention to provide a superior blood collection needle holder which facilitates the quick, safe and easy removal of used blood collection needles from the needle holder and replacement with a new blood collection needle if required.

It is yet a further object of the present invention to provide a blood collection needle holder which allows the used blood collection needle to be removed safely and without hazard of contact to the health car provider performing the procedure.

BRIEF DESCRIPTION OF THE DRAWINGS

FIG. 1 is a perspective view of the needle holder of the present invention illustrating one system for retaining the blood collection needle and releasing it from the holder in which an end of the holder opens laterally.

FIG. 2 is a perspective view of another blood collection needle holder of the present invention illustrating an optional means for retaining the laterally opened needle holder of FIG. 1 in a closed configuration.

FIG. 9 is a side view illustrating the needle holder of the present invention along with a specially adapted double ended needle.

FIGS. 10 and 11 are side cutaway views of the system of FIG. 9 illustrating in greater detail the blood collection needle retaining mechanism employed in this embodiment with the modified blood collection needle.

DETAILED DESCRIPTION OF THE INVENTION

Figure 3:
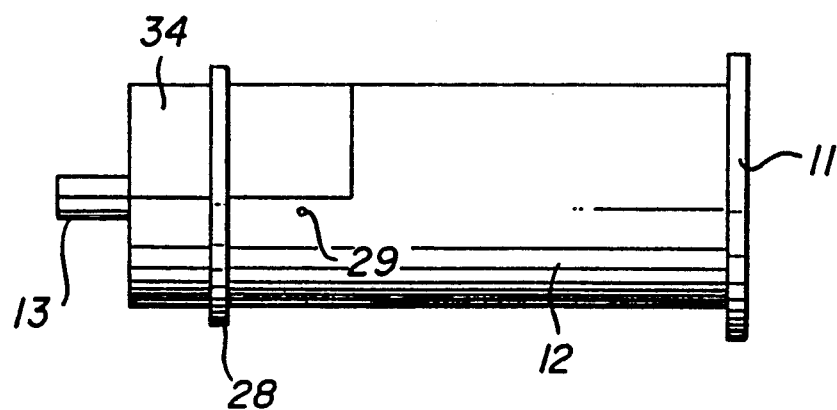
FIGS. 3 and 4 are side views of yet another embodiment of the present invention utilizing a needle holder which opens toward the end of the needle holder.

In accordance with the present invention, a blood collection system is provided having a needle holder with provision for rapidly and safely removing the blood collection needle from the holder without the need for complex manipulation or unscrewing of the needle. The blood collection needle holder of the invention comprises essentially an elongated tube open at one end for receiving a blood collection container such as a vacuum tube closed at one end with a penetrable rubber stopper and a locking means disposed at the other end for releasably holding the blood collection needle in communication with the collection container. The specific locking means which is employed to hold and release the blood collection needle in accordance with the invention can take several different forms as will be seen by having reference in detail to the drawings. However, in essence it consists of a collar which engages and holds the blood collection needle or a portion of a blood collection needle in proper alignment within the holder and which can quickly and easily be opened to eject the spent blood collection needle without the need for coming in contact with the needle or having to follow complex, time consuming procedures for disconnecting the needle from the holder.

The present invention will however be more fully appreciated by having reference to the drawings which illustrate various embodiments thereof.

Directing attention initially to FIG. 1 of the drawings, a tubular blood collection needle holder is shown at 12 generally having a configuration for accepting a blood collection container which is not shown in the drawings. One end 11 of the needle holder 12 is open to receive the blood collection container (not illustrated in this figure) and is provided with a flange. The other end of the holder 12 has a laterally hinged section 14 with a divided collar 13 projecting from the end of the needle holder. A simple retaining snap is provided at 15 on the side of the hinged section 14 to engage the mating snap 10 of the needle holder body 12 and hold the respective edges together in order to retain and hold the blood collection needle within the collar 13.

FIG. 2 of the drawings illustrates a similar holding mechanism to that shown in FIG. 1 except instead of providing a locking mechanism 15 in the form of a snap located on the side edge of the hinged portion of the needle holder, a simple sliding ring 28 is provided which can be moved over the end of the needle holder holding the needle to maintain the divided section 14 of the needle holder and the collar 13 in a closed position around the blood collection needle.

It will be appreciated that either form of closure used to hold the hinged portion of the holder in the locked position can quickly and safely be disengaged with the fingers of the hand holding the device.

Figure 4:
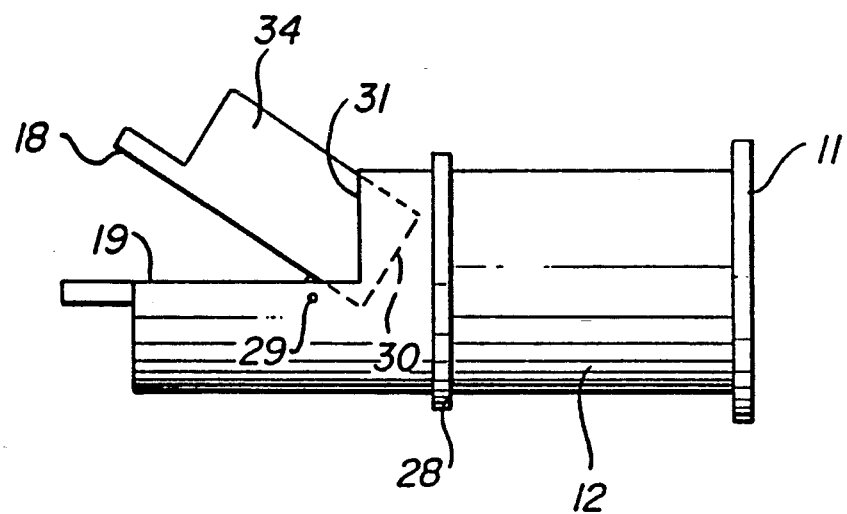

FIGS. 3 and 4 of the drawings illustrate an embodiment of the present invention in which the end of needle holder 12 which engages and holds the blood collection needle is divided along with collar 13 longitudinally into section 34 including neck portion 18. Section 34 of the holder is hinged to the body of the holder 12 at 29 so that it can be flipped open to disengage the top portion 18 of collar 13 from bottom half 19 to permit the blood collection needle to fall out of the holder. Sliding ring 28 functions to hold the halves of the end of the needle holder closed as heretofor described with respect to FIG. 2.

Figure 5:
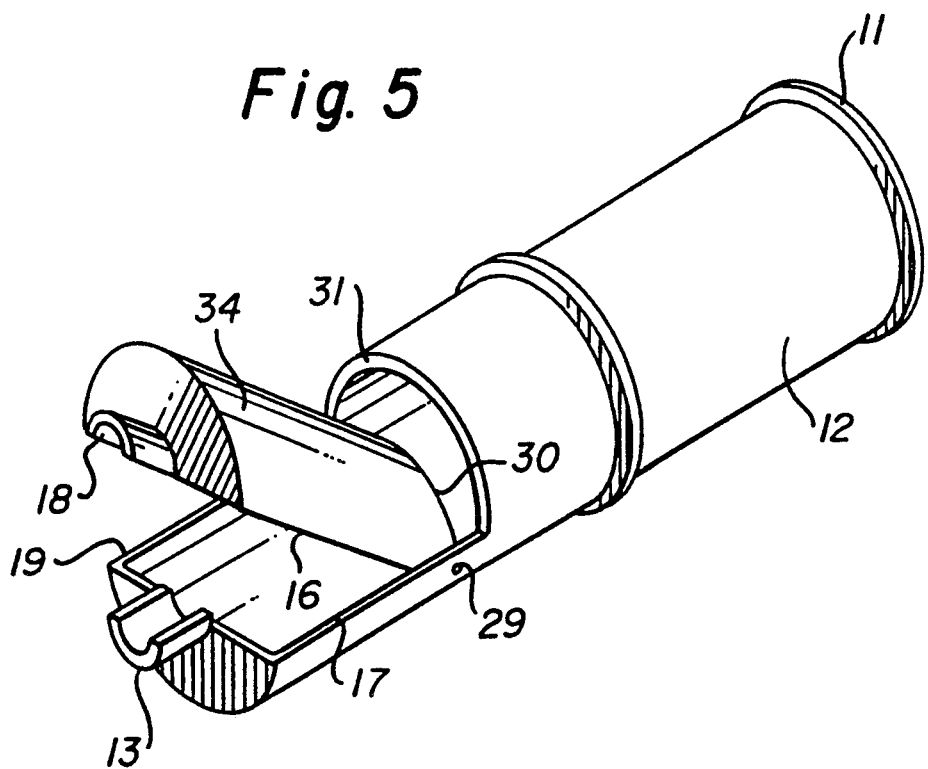
FIGS. 5 and 6 are perspective views illustrating respectively an embodiment of the present invention similar to that of FIGS. 3 and 4 in open and in closed configuration.
Figure 6:
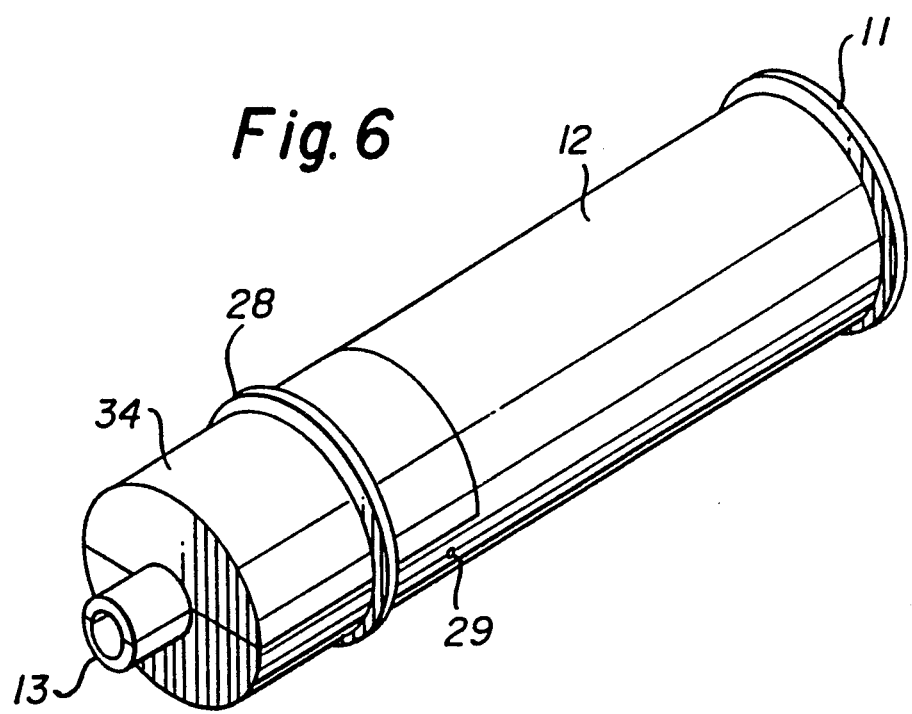

FIGS. 5 and 6 of the drawings illustrate an embodiment similar to that shown in FIGS. 3 and 4 in which an extended portion 30 is provided on the hinged portion 34, which can be depressed to facilitate ejection of the spent blood collection needle. A sliding ring 28 is provided to secure the hinged section 34 in the closed position shown in FIG. 6.

Figure 7:
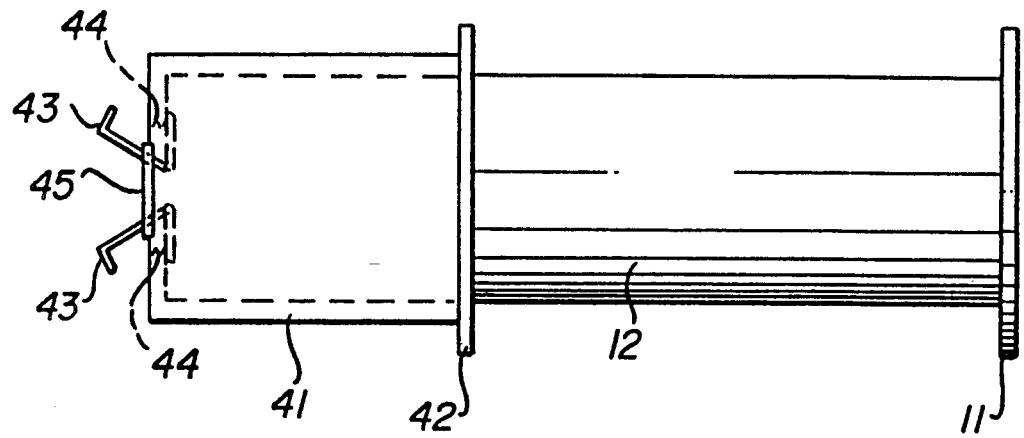
FIGS. 7 and 8 are side views respectively of an additional embodiment of the present invention wherein laterally opening jaws at the end of the needle holder are employed to retain the blood collection needle.
Figure 8:
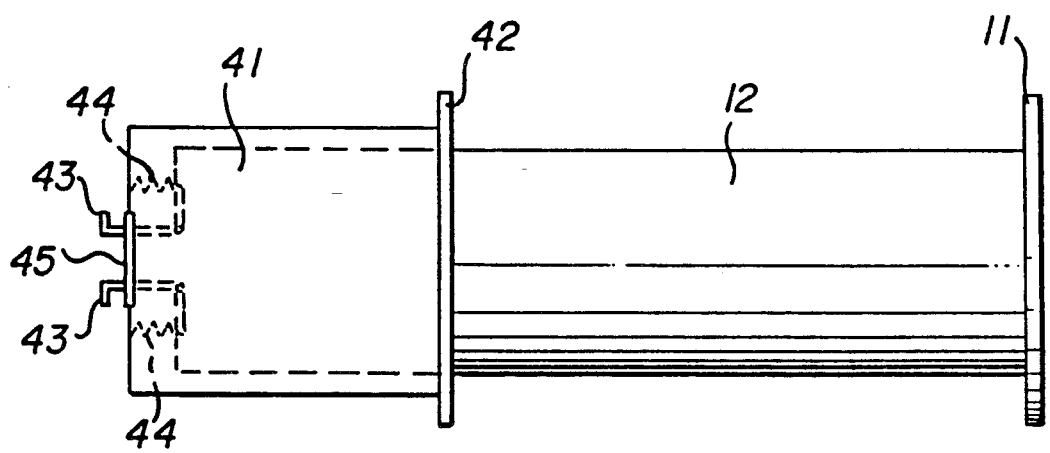

In FIGS. 7 and 8 of the drawings, yet another embodiment is illustrated in which a moveable sleeve 41 covers part of the needle holder body 12 at the end of the needle holder which holds the needle. The sleeve 41 has a flange 42 to facilitate moving the sleeve 41 slidably over the body of the holder 12. Three or more hinged jaws 43 are provided at opening 45 in the end of the sleeve to engage and hold a portion of the blood collection needle in place in the neck of the holder 12. Springs 44 are disposed between the end of the needle holder 12 and the end cap of moveable sleeve 41 to maintain section 41 in the position shown in FIG. 8 of the drawings such that the jaws 43 are forced laterally inward to engage and hold the blood collection needle. To remove the blood collection needle, sleeve section 41 is pushed back into the configuration shown in FIG. 7 of the drawings to release jaws 43 so that they are laterally displaced outward and allow the blood collection needle to fall out of engagement with the needle holder.

FIGS. 9, 10 and 11 of the drawings illustrate still another embodiment of the present invention in which a double ended blood collection needle is employed having a collar specifically adapted for use with a blood collection needle holder having a needle attachment collar 50 mounted at the end of the needle holder 12 which engages the blood collection needle 60. A blood collection container 64 is shown within holder 12. One end of double ended needle 60 penetrates stopper 65 after the other end of the needle is inserted into a vein. As shown in greater detail in FIGS. 10 and 11, the needle attachment 50 is essentially a sleeve which fits over the neck 63 of the blood collection needle holder 12. Collar 50 has a frame 51 and a movable section 56 provided with a flange 52. Small balls 53 are provided which move in and out of frame 51 and fit into depressions 61 which are radial grooves provided in the collar surrounding needle 62. Springs are provided at 54 to maintain section 51 in a forward position as shown in FIG. 10 so that indentation 57 in the frame is opposite the indentations provided in the blood collection needle collar and to maintain the balls 53 in partial engagement with the indentations in the needle collar. The position shown in FIG. 10 of the drawings thereby locks the needle into position within the attachment section 50. Sliding of the frame 51 backward into the configuration of FIG. 11 permits the ball 53 to slide out of engagement with depression 61 in needle collar thereby permitting the blood collection needle to fall from the attachment 66 is a stop to prevent the blood collection needle 60 from sliding freely into the needle holder 12. Once a new needle having a similar indented collar is inserted within the attachment, movement of the frame 51 to the left again forces the balls 57 down into the indentations 61 to engage and lock the needle in place. Removal and replacement of blood collection needles from the holder is thereby facilitated since the simple sliding movement of needle attachment collar backward with the fingers of one hand is all that is required to disengage the blood collection needle and replace it with a new one.

While various embodiments of the present invention have been shown and described herein for purposes of illustration, it will be apparent that other variations and embodiments are considered to fall within the scope of the defined invention.

What is claimed:

1. A blood collection needle holder comprising an elongated tube open at one end for receiving therein and holding a blood collection container, and locking means for releasable holding a blood collection needle in communication with said collection container disposed at the other end of said elongated tube, said locking means comprising a tubular receiver means for engaging said other end of the elongated tube and holding and retaining said blood collection needle in communication therewith, a sliding sleeve concentrically disposed around said receiver means and longitudinally displaceable with respect thereto, sufficient annular space being provided between said receiver means and sleeve to accommodate at least one laterally displaceable stop means disposed therein for engaging indentations provided in a collar fixedly attached to the portion of said blood collection needle to be disposed within said receiver, said sleeve being further provided with means for engaging and laterally displacing said stop means partially into said indentations when said sleeve is displaced longitudinally in a closed position with respect to said receiver means to thereby engage and hold said needle within said means and to release said needle when said sleeve is retracted.

2. The needle holder of claim 1 wherein said indentations are a single continuous groove in said blood collection needle collar.

3. The needle holder of claim 1 wherein said stop means are one or more balls of sufficient size to partially fit in said indentations when displaced therein.

4. A blood collection needle holder for holding a disposable blood collection needle and blood collection container comprising an elongated tube open at one end for holding said container and fitted at its other end with means for releasably holding said needle in communication with said container, said needle holding means comprising a tubular receiver means for engaging said other end of the elongated tube and holding and retaining said blood collection needle in communication therewith, a sliding sleeve concentrically disposed around said receiver means and longitudinally displacable with respect thereto, sufficient annular space being provided between said receiver means and sleeve to accommodate at least one laterally displacable stop means disposed therein for engaging indentations provided in a collar fixedly attached to the portion of said blood collection needle to be disposed within said receiver, said sleeve being further provided with means for engaging and laterally displacing said stop means partially into said indentations when said sleeve is displaced longitudinally in a closed position with respect to said receiver means to thereby engage and hold said needle within said means and to release said needle when said sleeve is retracted.

* * * * *